United States Patent [19]

Rothfuss et al.

[11] Patent Number: 4,610,383
[45] Date of Patent: Sep. 9, 1986

[54] DISPOSABLE LINEAR SURGICAL STAPLER

[75] Inventors: Robert G. Rothfuss, Bellevue, Ky.;
Federico Bilotti, Madeira, Ohio;
Hector Chow, Cincinnati, Ohio; J.
Charles Hueil, Loveland, Ohio;
Narinderjit S. Sambi, Batavia, Ohio

[73] Assignee: Senmed, Inc., Cincinnati, Ohio

[21] Appl. No.: 542,122

[22] Filed: Oct. 14, 1983

[51] Int. Cl.⁴ ............................................. A61B 17/00
[52] U.S. Cl. ................................. 227/19; 128/334 R;
227/DIG. 1
[58] Field of Search ............... 128/334 R, 334 C, 335;
227/DIG. 1, 19, 155, 156, 83

[56] References Cited

U.S. PATENT DOCUMENTS

| | | | |
|---|---|---|---|
| 960,300 | 6/1910 | Fischer | 227/DIG. 1 X |
| 2,344,071 | 3/1944 | Wilson et al. | 227/DIG. 1 X |
| 3,079,606 | 3/1963 | Bobrov et al. | 227/DIG. 1 X |
| 3,080,564 | 3/1963 | Strekopitov et al. | 227/DIG. 1 X |
| 3,252,643 | 5/1966 | Strekopytov et al. | 227/DIG. 1 X |
| 3,269,630 | 8/1966 | Fleischer | 227/DIG. 1 X |
| 3,275,211 | 9/1966 | Hirsch et al. | 227/DIG. 1 X |
| 3,315,863 | 4/1967 | O'Dea | 227/DIG. 1 X |
| 3,490,675 | 1/1970 | Green et al. | 227/DIG. 1 X |
| 3,499,591 | 3/1970 | Green | 227/DIG. 1 X |
| 3,589,589 | 6/1971 | Akopov | 227/DIG. 1 X |
| 3,638,652 | 2/1972 | Kelley | 227/DIG. 1 X |
| 4,379,457 | 4/1983 | Gravener et al. | 227/DIG. 1 X |
| 4,383,634 | 5/1983 | Green | 227/DIG. 1 X |
| 4,422,567 | 12/1983 | Haynes | 227/19 |
| 4,485,817 | 12/1984 | Swiggett | 227/DIG. 1 |

FOREIGN PATENT DOCUMENTS

| | | |
|---|---|---|
| 406832 | 12/1924 | Fed. Rep. of Germany . |
| 3214810 | 4/1982 | Fed. Rep. of Germany . |

OTHER PUBLICATIONS

"Aseptic Technic of Stomach Resections" by A. De-Petz, *Annuals of Surgery*, pp. 388–392.
"Gastric Resection with the DePetz Mechanism", by M. L. Weinstein & E. Lawrence Adams, *American Journal of Surgery*, vol. LVIII, No. 2, pp. 202–206.
"DePetz Clamp in Surgical Treatment of Gastric Cancer", by G. T. Pack and I. M. Scharnagel, *American Journal of Surgery*, Mar. 1936, pp. 575–581.

Primary Examiner—Paul A. Bell
Attorney, Agent, or Firm—Wood, Herron & Evans

[57] ABSTRACT

A disposable linear surgical stapler includes a handle, anvil, staple cartridge and flexible shaft attaching the handle to the cartridge and transmitting a firing force exerted at the handle to the distant cartridge for sequentially implanting, forming and clinching staples in two staggered staple lines. A flexible cable in the flexible shaft pulls a firing wedge across a plurality of staple drivers in the cartridge. The anvil is adjustable to vary the gap between the anvil and staple cartridge.

34 Claims, 12 Drawing Figures

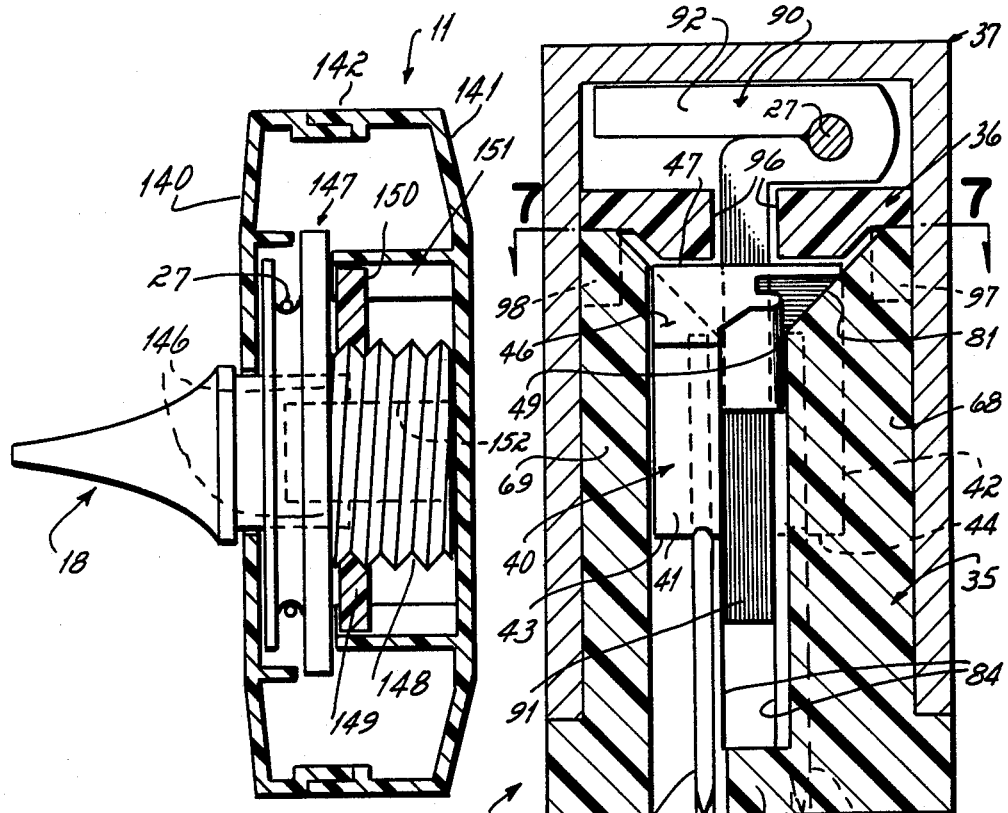
FIGURE 4
FIGURE 5
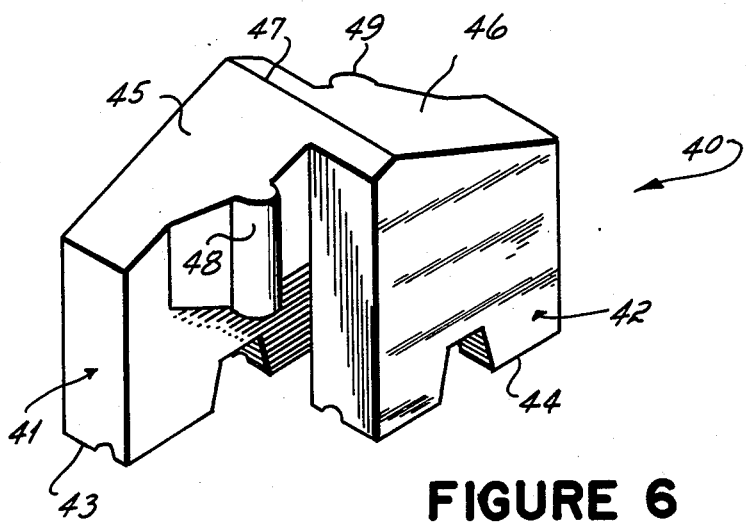
FIGURE 6

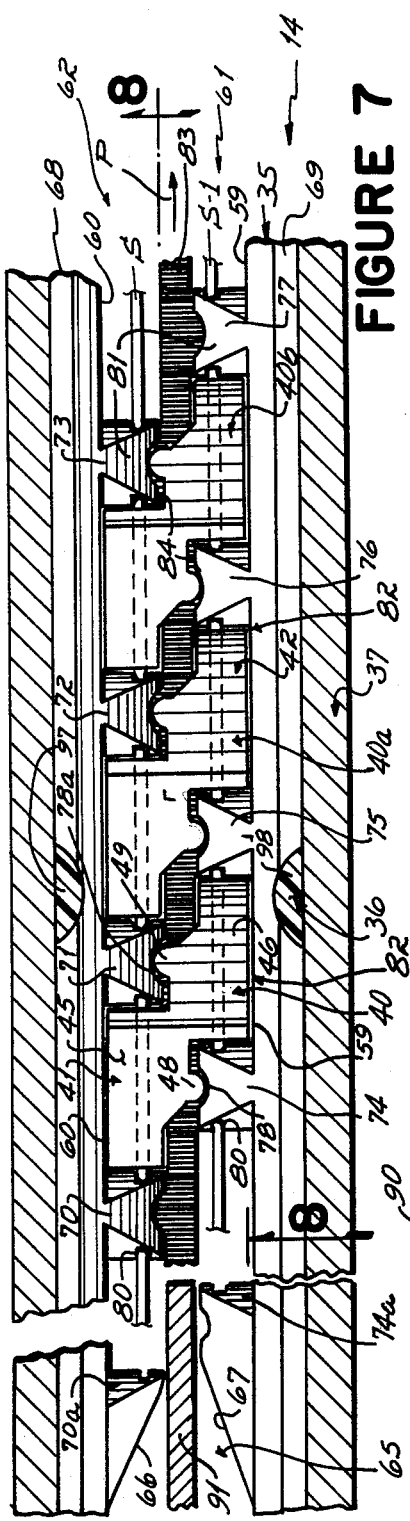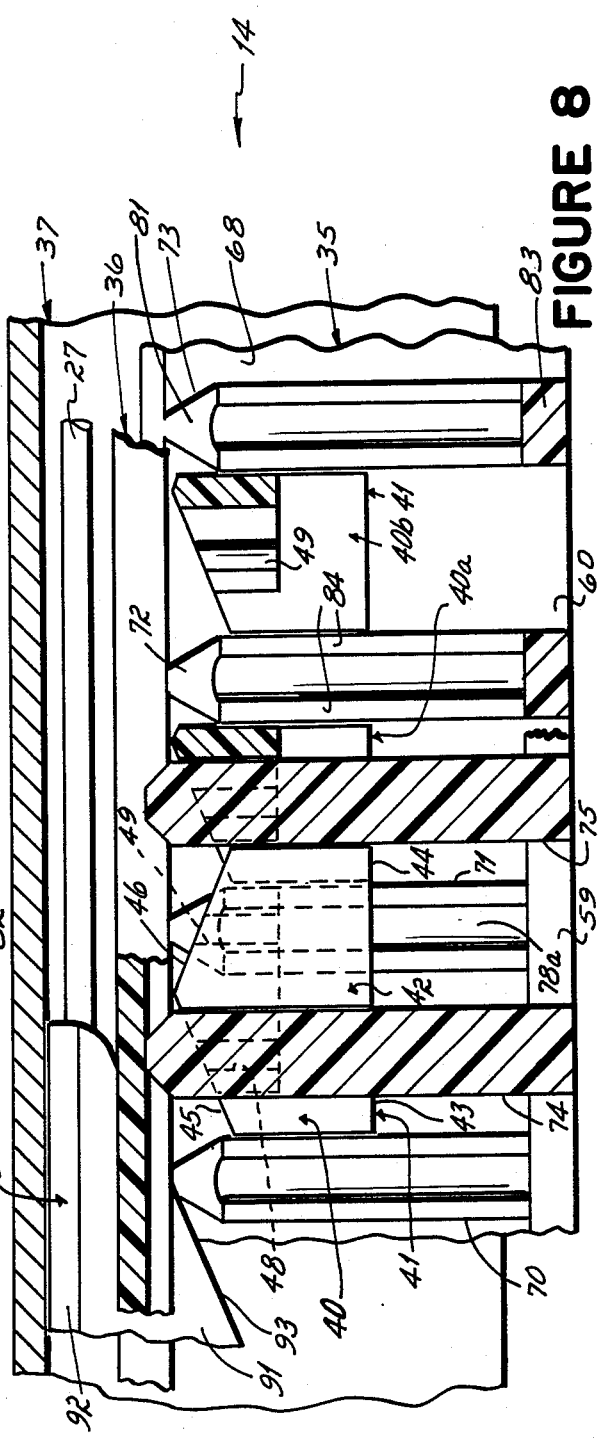

DISPOSABLE LINEAR SURGICAL STAPLER

This invention relates to a disposable linear surgical stapler, and more particularly to an improved linear surgical stapler for implanting staples into tissue.

In recent years, an important medical trend has been the substitution of staples for conventional sutures in surgical procedures. Such staplers have simplified many procedures which were difficult to accomplish manually. Also, the use of surgical staplers has significantly reduced the time required for many procedures and thus reduced the time required for maintaining a patient under anesthetic.

Linear surgical staplers for implanting a row of staples have been in use for some time. One early linear stapler, such as that shown in U.S. Pat. No. 3,080,564, included a permanent, rigid shaft, multi-use device wherein staples were manually loaded one-by-one. While such staplers performed well in a multiplicity of uses, they were complex in construction, expensive to manufacture, heavy, bulky, and difficult to load with staples. They also required continuous maintenance, cleaning and sterilizing after each use.

Improvements to such staplers included improved reloading features such as those shown in U.S. Pat. Nos. 3,275,211 and 3,589,589. These improvements included the use of presterilized, disposable loading units or staple cartridges. While these improvements significantly reduced the time previously required for hand-loading of the staples, the basic instrument still had to be disassembled, cleaned, reassembled, and sterilized for each procedure. These staplers also required frequent maintenance and adjustment.

Recently, rising hospital costs have generated an increasing interest in disposable surgical staplers. Disposable staplers are designed to eliminate as much work as possible (i.e., disassembly, cleaning, reassembly, sterilization, maintenance and adjustments), while not compromising surgical procedures, and improving overall efficiency.

One such disposable stapler is shown in U.S. Pat. No. 4,383,634, for example. These staplers generally perform well. However, since the forward-most anvil-carrying jaw is pivoted, the anvil and cartridge may not approach each other in parallel relationship, making only a single gap setting achievable. Stated in another way, since the anvil and cartridge are pivoted at one end, there is only one position in which they are parallel to each other as they are pivoted. This permits only one gap setting for tissue as any other would produce a varying gap along the staple line due to a diverging orientation of the anvil and cartridge. This in turn would result in staples having formed legs of varying length along the suture line.

To provide disposable staplers having differing gaps, manufacturers have simply supplied different staplers. Such staplers are frequently provided in a "tight" suturing version with short legged staples, and a "loose" suturing version, with staples having longer legs. The surgeon selects the appropriate stapler for the particular procedure in process.

These aforementioned staplers have another difficulty inherently residing in their own rigid structures. While useful in many applications, it is often difficult to orient the stapler so as to implant a line of staples in exactly the right direction. Also, in some instances, it may be difficult to even apply the stapler to the tissue to be stapled in view of the tissue lying in limited access areas where it is difficult to place or maneuver the entire stapler.

Accordingly, it has been one objective of this invention to provide an improved disposable linear surgical stapler, overcoming these difficulties previously associated with disposable staplers.

A further objective of the invention has been to provide an improved disposable linear surgical stapler providing a plurality of tissue gap settings over which a plurality of single-size staples can be properly implanted and formed.

A further objective of the invention has been to provide an improved disposable linear surgical stapler useful in limited access areas and wherein an anvil and staple cartridge apparatus can be oriented in such area independently of, and spaced from, the position of the operating handle for the stapler.

To these ends, a preferred embodiment of a disposable linear surgical stapler according to the invention includes a staple cartridge and anvil pivoted together, an operating handle substantially independent of the cartridge and anvil, and a flexible stapler operating shaft operably interconnecting the handle and the stapler cartridge. The flexible shaft includes a cable within a flexible conduit and is operable to transmit an operating force, applied at the handle, to the staple cartridge for driving staples through tissue and against the aligned anvil.

An anvil is provided with a gap control apparatus for adjusting the distance between the staple cartridge and anvil, after the two components are aligned and latched, so that a plurality of single size staples can be uniformly implanted and formed along a staple line and over a plurality of gap settings.

A one-way rotatable firing knob is provided on the handle and is connected through the cable to a firing wedge in the staple cartridge. The firing wedge is pulled along a line of staple drivers to sequentially fire staples toward the anvil, through the tissue to be sutured, and against the anvil.

The anvil includes a plurality of staple clinching pockets configured to form and clinch staples over at least two discrete gaps between the anvil and staple cartridge.

A one-way start apparatus is utilized to prevent firing knob rotation in the wrong direction.

In order to insure proper anvil and staple cartridge alignment, the staple cartridge is provided with an alignment pin and a latch lug, both of which are received and held in alignment receiving pockets within ends of the anvil apparatus. The latch lug is releasable to permit selective opening of the anvil and cartridge jaws.

Accordingly, it will be appreciated that the improved disposable linear surgical stapler can be utilized in limited access areas, the relatively small anvil and cartridge end being easily oriented in small areas, while the handle remains outside such areas, and connected to the cartridge only by the cable and flexible conduit.

Moreover, the stapler provides different tissue gap settings for single size staples, and operation of the stapler is facilitated by sequential staple firing.

These and other objects and advantages will become readily apparent from the following detailed description of a preferred embodiment of the invention, and from the drawings in which:

FIG. 4 is a cross-sectional view taken along lines 4—4 of FIG. 3;

FIG. 5 is a cross-sectional view taken along lines 5—5 of FIG. 3;

FIG. 6 is an enlarged view of a staple driver;

FIG. 7 is a cross-sectional view taken along lines 7—7 of FIG. 5;

FIG. 8 is a cross-sectional view taken along lines 8—8 of FIG. 7;

Figure 1:
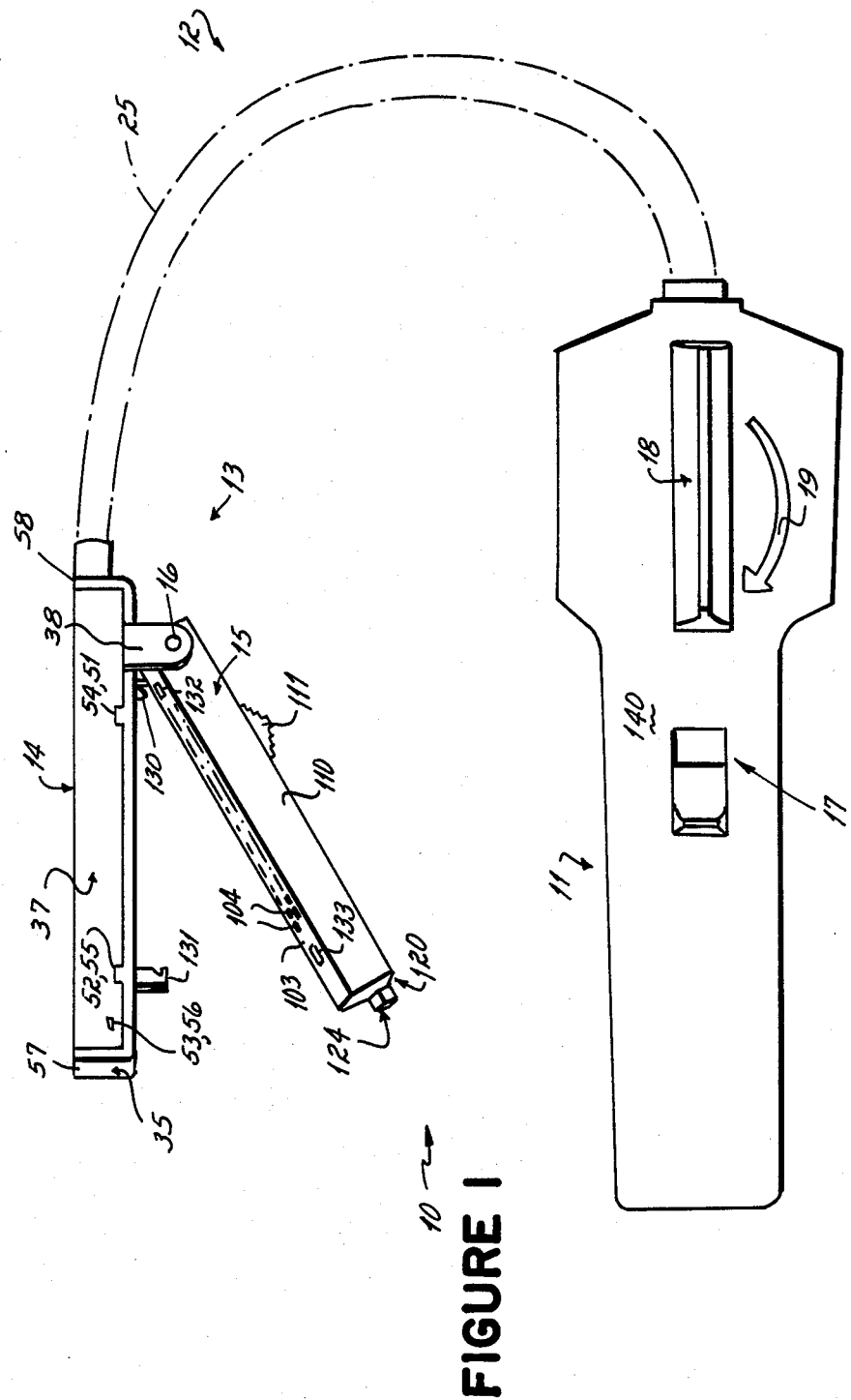
FIG. 1 is a pictorial view of a disposable linear surgical stapler according to the invention, and showing the anvil and staple cartridge pivoted apart.

Turning now to the drawings, there is shown in FIG. 1 a disposable linear surgical stapler 10 according to the invention. The stapler 10 includes a handle 11, an elongated flexible shaft 12 and a cartridge/anvil structure 13, including a cartridge means 14 and an anvil means 15 pivoted to each other at pivot point 16.

The stapler 10, according to a preferred embodiment of the invention, is useful for implanting two staggered rows of staples in tissue or organs such as those disposed in the alimentary canal or digestive tract. In general, and as will be further appreciated, the tissue is clamped in a gap G between the cartridge means 14 and the anvil means 15. A safety 17 in handle 11 is then retracted to the position shown in FIG. 1, and firing knob 18 is rotated in the clockwise direction of arrows 19 in order to implant the staggered rows of staples in the tissue.

The utilization of the flexible shaft 12 permits the cartridge/anvil structure 13 to be oriented independent of the handle 11, with the flexible shaft operatively connecting the staple cartridge means 14 and the handle 11 for the implantation of staples, while removing the necessary apparatus of the handle 11 from immediately adjacent the tissue site in a surgical procedure.

FLEXIBLE SHAFT

Figure 2:
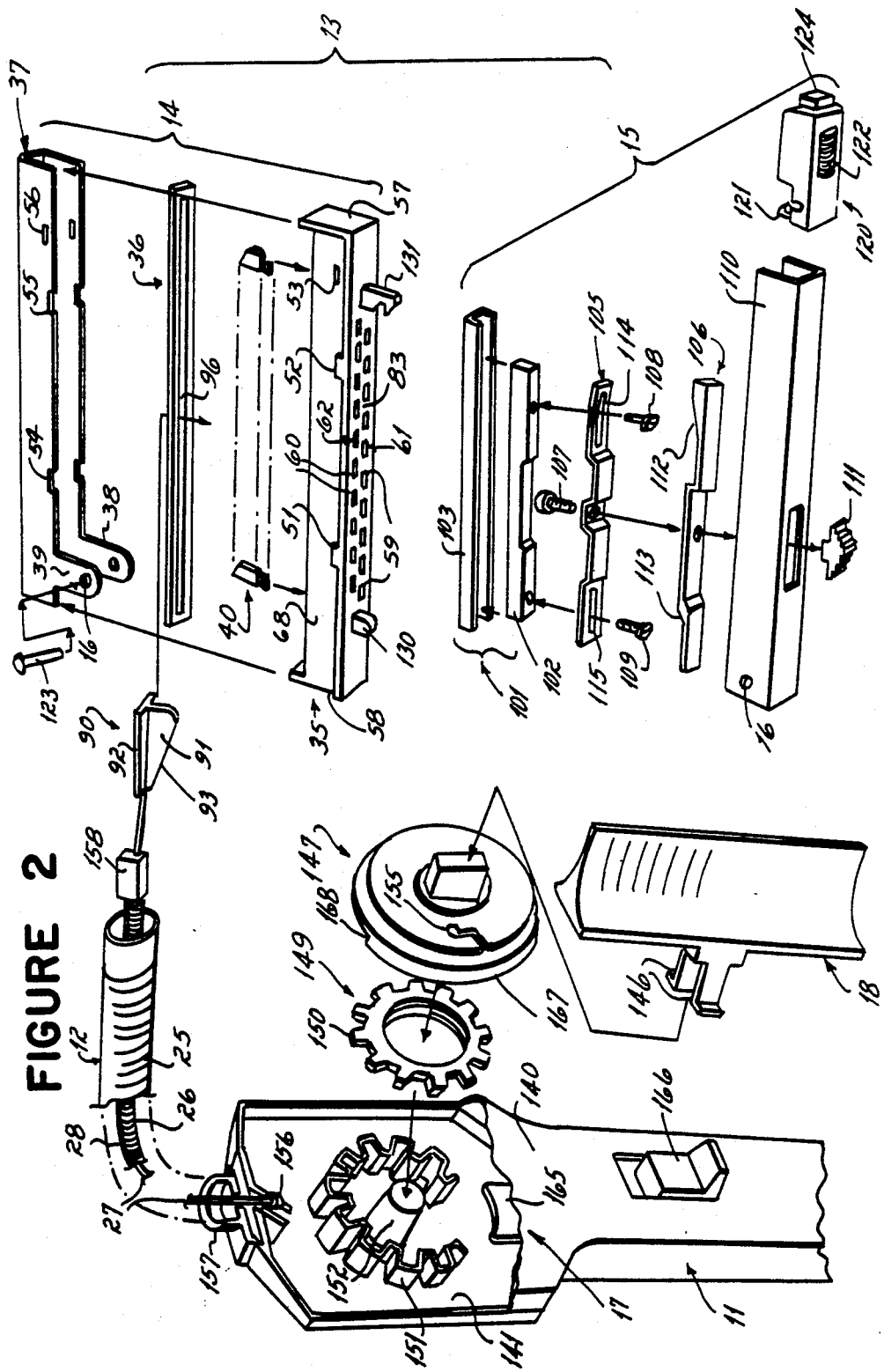
FIG. 2 is an exploded perspective view of components of the stapler of FIG. 1.
Figure 3:
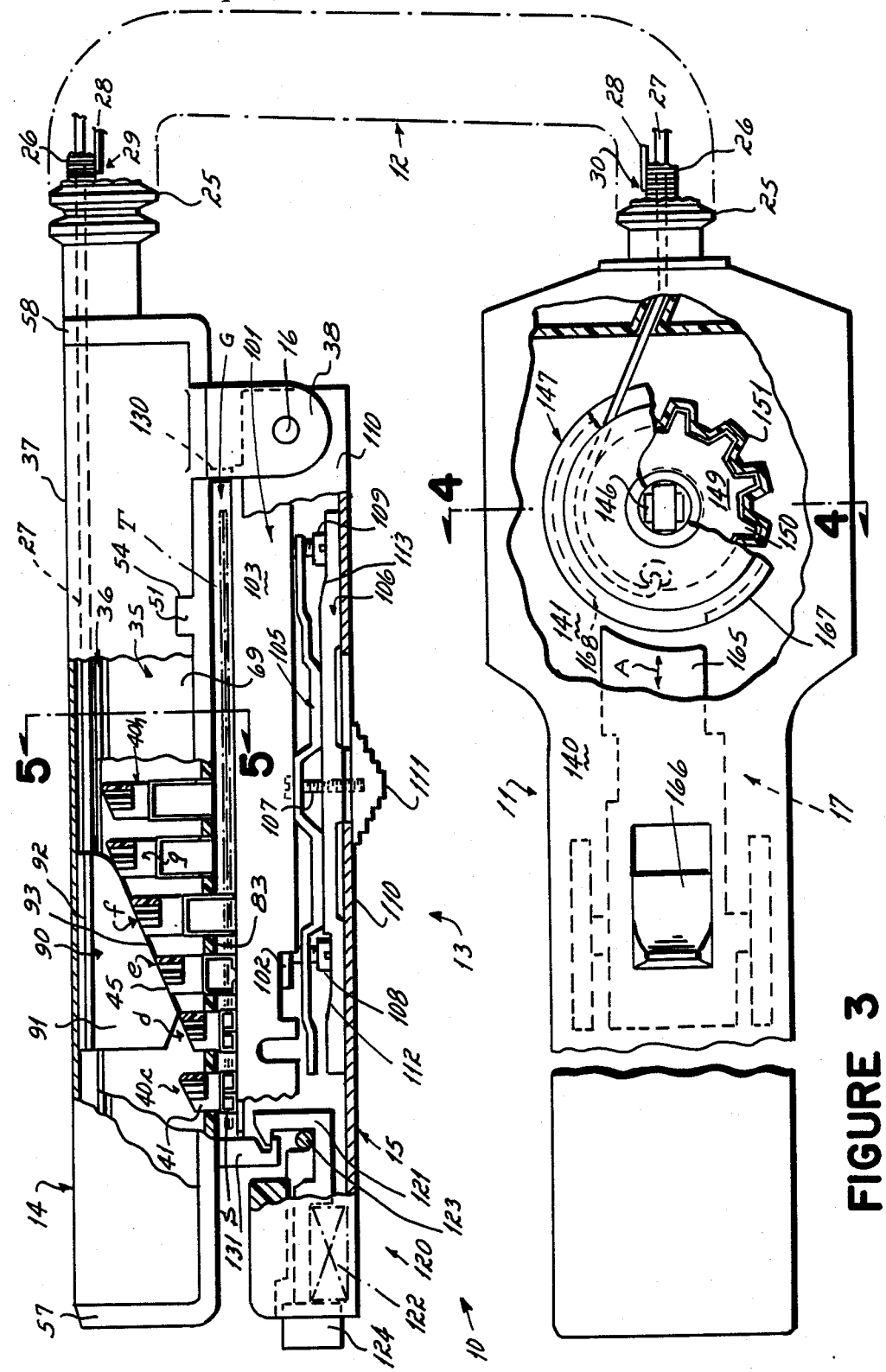
FIG. 3 is a partially broken elevation view of the stapler of FIG. 1, showing the anvil and staple cartridge latched together.

Referring now to FIGS. 2 and 3, the flexible shaft 12 includes a flexible corrugated outer covering 25, a flexible conduit 26 and a flexible cable 27 slidably disposed within the conduit 26. Conduit 26 is preferably formed of spirally wrapped wire defining an open interior passageway.

Also included in the flexible shaft 12 is a flexible tension wire 28 preferably attached to the flexible conduit 26 along the length thereof. Tension wire 28, by virtue of its connection to the flexible conduit 26, prevents undesirable firing of the stapler due to inadvertent extensions of the flexible conduit 26.

Flexible tension wire 28 has a foward end 29 which is connected to the anvil/staple structure 13 and a rearward end 30 which is connected to the handle 11. The forward and rearward ends 29 and 30 of the flexible tension wire 28 are secured to the cartridge means 14 and the handle 11 respectively by any suitable means. Outer covering 25 serves as a flexible, sterilizable covering for the conduit 26 and provides a barrier between the metal conduit and surrounding tissues which otherwise might get pinched in the spring-wound conduit.

STAPLE CARTRIDGE

Details of the various components and features of the stapler 10 are perhaps seen best in FIGS. 2 and 3, with occasional reference to FIGS. 4–8. Turning now to FIG. 2, various components of the stapler 10 are shown in exploded perspective form for the purposes of clarity of description. The cartridge/anvil structure 13 includes a cartridge means 14 and an anvil means 15.

The cartridge means 14 includes a cartridge body 35, a cartridge lid 36, and a catridge support channel or housing 37. Cartridge support channel 37 is provided with lugs 38 and 39, defining a pivot line 16 about which the cartridge means 14 and anvil means 15 are pivoted together.

Within cartridge body 35 are disposed a plurality of staple drivers 40, the structure of which is best seen in FIG. 6. These drivers are substantially identical and for clarity will be referred to by the numeral 40 or by the numeral 40 followed by a letter where differentiation is necessary. Staple drivers 40 have lower bifurcated portions forming respective staple driving legs 41 and 42, which are offset with respect to each other. A top view of the drivers 40 as in FIG. 7 illustrates the offset nature of the respective legs of the drivers 40.

Each leg 41, 42 has a respective staple-engaging end 43, 44, and the legs 41 and 42 are joined at their upper ends, forming cam surfaces 45 and 46 which taper upwardly to form an apex 47 centrally of the driver 40. Driver leg 41 also includes an elongated guide rib 48, while leg 42 includes an elongated guide rib 49, which ribs extend downwardly from the respective cam surfaces 45 and 46. As will be appreciated, the respective driver legs 41 and 42 are operative to engage and fire staples in two offset or staggered rows. To this end, it will be further noted that leg 41 slightly overlaps leg 42. It will also be noted that actuation of a single driver 40 will be operable to drive two staples at the same time by means of legs 41 and 42 operating on a staple in each of the staggered rows.

Returning now to the cartridge means 14, it will be appreciated that the body 35 and the housing 37 are provided with respective projections and detents, such as those projections 51, 52 and 53, and respective detents 54, 55 and 56, for positioning and holding the housing 37 on the cartridge body 35 when the stapler is assembled. Moreover, it will be appreciated that the cartridge body 35 has a foward end 57 and a rearward end 58.

Also, it will be appreciated that cartridge body 35 is provided with a plurality of staple-ejecting apertures 59 making up one staple row, and staple ejecting apertures 60 making up a second, staggered staple row. Staple-ejecting apertures 59 lie in one row 61, while staple-ejecting apertures 60 lie in an adjacent, parallel but staggered row 62, the apertures 60 being staggered by approximately one-half staple width from the apertures 59 in the row 61. The rows 61, 62 in the preferred embodiment are about 60 millimeters in length, but it shall be appreciated that other size staplers according to the invention can be made, such as in staple row lengths of 90 millimeters and 120 millimeters, for example.

Turning now to further details of the cartridge means 14, attention is directed to FIGS. 3, 5, 7 and 8. FIG. 7 is a partial cross-sectional view looking down into the cartridge body 35 from a position above the drivers 40 depicted in FIG. 7 as drivers 40, 40a and 40b, each of which is similar in construction.

The lefthand side of FIG. 7 corresponds generally to the forwardmost end 57 of the cartridge means 14 and includes a wedge pocket area 65. Tapered surfaces 66 and 67 define a rearward end of the wedge pocket 65 and serve as guiding surfaces as will be described.

The cartridge body 35 comprises elongated side walls 68 and 69. A plurality of elongated vertical projections, or guide rails, 70 through 73 extend from the side wall 68 toward the opposite side wall, while an offset plurality of elongated rectangular projections 74 through 77 extend from the opposite side wall 69 toward the side wall 68. The guide rails are essentially identical, except the forwardmost guide rail 70a differs from the other guide rails in the provision of the tapered surface 66 adjacent wedge pocket 65. Guide rail 74 differs from the other guide rails by virtue of the tapering surface 67 at the rearward end of the wedge pocket 65.

The guide rails 70 through 77 are provided with curved driver guiding surfaces such as that shown at 78 in guide rail 74. These curved or concave surfaces extend longitudinally of the guide rails for reception of the guide ribs 48, 49 of the drivers 40. For example, as shown in FIG. 7, guide rib 48 extends into the concave guide surface 78, while the guide rib 49 of the same driver extends into the concave guide surface 78a of the guide rail 71.

The guide rails 70 through 77 are provided with elongated staple channels 80 for receiving staples "S" or "S-1" beneath the drivers. These staples preferably have legs about 4.0 to 5.0 millimeters in length and are formed of wire about 0.009" to 0.011" in diameter, although other sizes and shapes may also be useful. The staples S and S-1 are slightly wider than the respective driver legs, and thus ends of the staples S and S-1 are shown in the view of FIG. 7 extending outwardly from beneath the driver legs.

Each of the guide rails 70 through 77 include an upper tapered surface, such as at 81, which tapers from the respective side walls 68, 69 downwardly toward the bottom of the cartridge. At the righthand edge of FIG. 7, the driver has not been shown in order to clearly illustrate the staples S and S-1 and their disposition within the cartridge body 35. It will be appreciated that the respective guide rails 70 through 77 define driver receiving channels for reception of the respective drivers. For example, rails 71 and 72 define therebetween a portion of a driver receiving channel 82 for the leg 41 of the driver 40a, while the rails 75 and 76 define another offset portion of the same driver receiving channel for receiving the leg 42 of the driver 40a.

In FIG. 7 a single row 62 of staples S is shown at an upper portion of the figure, while another row 61 of staples, S-1, is shown at a lower portion of the figure. It will be appreciated then that the legs 41 of the respective drivers are disposed over a row 62 of staples S, while the respective legs 42 of the same drivers are disposed over a row 61 of staples S-1.

At the bottom of the driver channels 82, an elongated rib 83 is provided for closing off the bottom of the cartridge body 35 to prevent the drivers from falling out of the cartridge body 35.

Finally, it should further be noted that each rail includes a forward face 84 facing the opposite wall 68 and 69 of the cartridge body 35. These generally flat faces 84 surround the respective concave surfaces 78 and define a path "P" as will be further described.

In summary, then, the respective drivers 40 are slidably received within driver receiving channels 82, while the respective staples S and S-1, in their respective staggered rows, are received in the staple channels 80 beneath the drivers and in position for driving outwardly of the cartridge body 35 when the drivers are actuated against the staples.

A wedge 90 is disposed within the cartridge body 35, as will now be described. Wedge 90 includes a wedge blade 91 and a wedge base 92. Wedge blade 91 has a lower wedging surface 93 for engaging the cam surfaces 45 or 46 of the respective drivers 40 to drive them against the staples and fire the staples from the cartridge body 35.

Preferably, the wedge 90 is metallic and base 92 is crimped about the cable 27, as shown in FIG. 5. Alternately, of course, the wedge itself could be molded from any suitable material and attached to the cable 27 in any suitable manner.

Wedge 90 is originally disposed in the wedge pocket 65 at forward end 57 of the cartridge body 35. Guide surfaces 66 and 67 function to guide wedge blade 91 into path P, between rails 70-77 and are elongated in a direction normal to wedge movement.

The operation of the wedge surface 93 against the respective drivers is perhaps best seen in FIG. 3, where it can be appreciated that the wedge surface 93 has already engaged and pushed drivers 40c and 40d downwardly. Moreover, it will be appreciated that the surface 93 has further engaged drivers 40e, 40f and 40g and pushed them against the staples to varying extents. Driver 40h has not yet been contacted by the wedge surface 93.

In this regard, it will be further appreciated that the operation of the respective drivers, such as driver 40c for example, is operative to fire staples S-1 (not shown in FIG. 3) and S outwardly of the cartridge body 35 and against the anvil means 15 in two staggered rows. Only the row 62 of staples S is shown in FIG. 3. Thus, when wedge 40c has been activated by the wedge 90, for example, a staple S is formed and clinched as shown FIG. 3, and an offside staple S-1 (not shown) is also formed and clinched by operation of the driver 40c, and so on for each of the drivers in the cartridge body 35. Thus, a staple S-1 is fired simultaneously to a staple S in another row, however, the drivers are engaged sequentially so staples in the same row are fired, formed and clinched sequentially.

In order to capture the drivers 40 within the cartridge body 35, and in order to provide a guide for the wedge 90, cartridge lid 36 is disposed along the top of the cartridge as shown in FIGS. 5 and 8. Cartridge lid 36 is provided with a slot 96 for receiving the blade 91 of the wedge 90. Furthermore, the lid 36 is provided with projections 97 and 98, for example, for securing the cartridge lid 36 on the cartridge body 35 while also maintaining proper spacing between cartridge walls 68 and 69.

The housing 37 is disposed over the cartridge body 35 and serves to slidingly capture the wedge 90 between the cartridge lid 36 and the housing 37 so that the wedge is free to slide through the slot 96 and within the path P (FIGS. 5 and 7) in order to engage the respective drivers 40 to fire staples S and S-1.

It should be appreciated that the cartridge body 35, including walls 68, 69, rails 70–77 and rib 83 are preferably formed from an integral molding of any suitable material such as plastic.

ANVIL

Returning now to FIGS. 2 and 3, anvil means 15 will now be described in detail. The anvil means 15 comprises an anvil block 101 including an anvil insert 102 and an anvil 103 containing a series of staple pockets 104 for forming and clinching staples, such as shown in FIG. 3. Pockets 104 are shown in FIG. 1.

As mentioned above, the anvil 103 is adjustable in order to provide different sized gaps G. In particular, a sliding retention plate 105 is disposed between the insert 102 and a cam plate 106. A screw 107 captively secures the retention plate 105 and the cam plate 106 within an anvil support channel 110 by a threaded connection to a manually operable slide switch 111, while two screws 108 and therefor 109 secure the slide plate 105 to the insert 102.

As best seen in FIG. 3, the cam plate 106 is provided with cam surfaces 112 and 113. Accordingly, and as shown in FIG. 3 for example, the anvil 103 can be extended outwardly of the anvil means 15 toward cartridge means 14 by sliding the retention plate 105 and the cam plate 106, as a unit. For example, and as shown in FIG. 3, the anvil 103 is in a retracted position. The heads of screws 108 and 109 reside on lower portions (as viewed in FIG. 3) of the respective cam surfaces 112 and 113. However, when slide switch 111 is engaged and moved to the right, as viewed in FIG. 3, it will be appreciated that the retention plate 105 and cam plate 106 also slide to the right and the heads of screws 108 and 109 ride up the respective cam surfaces 112 and 113 to a higher portion thereof, thereby extending the anvil 103 outwardly and toward the cartridge means 14.

Of course, it will be appreciated that the screws 108 and 109 extend through slots 114 and 115 respectively in the plate 105, while screw 107 secures together the plate 105, the cam plate 106 and the sliding switch 111. If desired, respective projections and detents can be provided in the mating faces of the plate 105 and cam plate 106 to prevent their movement with respect to each other.

It will also be appreciated that the position of the anvil 103 can be adjusted by means of adjusting the screws 108 and 109. For example, it is desirable to produce an anvil surface which is parallel to the cartridge means 14 when the anvil means 15 is latched to the cartridge means 14. Accordingly, and during manufacture of the invention, the screws 108 and 109 can be adjusted to a predetermined extension so that they produce, in combination with the cam plate 106, a parallel positioning of the anvil 103 with respect to both the entire anvil means 15 and the cartridge means 14.

Accordingly, it will be appreciated that the anvil means 15 provides an extensible anvil which is capable of defining at least two different gaps between the cartridge means 14 and the anvil means 15. A larger gap G is provided when the screws 108 and 109 reside in lower portions of the cam plate 106, and a smaller gap is produced when the cam plate 106 is moved so that the cam surfaces 112 and 113 engage the screws 109 and 108, respectively, to project the anvil outwardly of the anvil means 15, all while maintaining the anvil 103 in parallel relationship to the anvil means 15 and to the cartridge means 14, to provide a uniform gap G for whatever gap is selected.

Anvil means 15 is also provided with a cartridge means latch 120 mounted within the anvil support channel 110. The cartridge means latch 120 is perhaps best shown in FIG. 3 and includes a spring-loaded extensible latch member 121 urged by spring 122 in a forward direction, or to the left as viewed in FIG. 3, and against the stop which comprises a rivet 123. An actuating button 124 extends outwardly of the latch 120 and is manually operable to push the latch member 121 in a rearward direction, or to the right as viewed in FIG. 3, to unlatch the cartridge means 14, as will be described.

Of course, it is desirable to operably align the cartridge means 14 with the anvil means 15 and as well to latch the cartridge means 14 to the anvil means 15. In this regard, the preferred embodiment of the invention includes means for appropriately aligning, both longitudinally and laterally, the cartridge means 14 with the anvil means 15. As shown in FIG. 2, the cartridge body 35 is provided with a positioning lug 130 and a combination positioning and latching lug 131. Moreover, the anvil 103 is provided with positioning recesses 132 and 133 therein for receiving the respective lugs 130 and 131. Accordingly, when the cartridge means 14 and the anvil means 15 are pivoted together about pivot point 16, the lug 130 is received within the recess 132 and the combination positioning and latching lug 131 is received within the recess 133, the recess surfaces guiding and positioning the respective lugs, and thus maintaining the cartridge means 14 and anvil means 15 in aligned condition.

Also, it will be appreciated that the lug 131 includes a detent for engaging with an upper detent portion of the latch member 121 of the latch 120. As the lug 131 is received within the recess 133, it engages the latch member 121, pushes it rearwardly, and thereafter permits the latch member to move forwardly, holding the lug 131 within the anvil means 15 and thus latching the cartridge means 14 and the anvil means 15 together.

HANDLE

Turning now to FIGS. 2, 3 and 4, the handle will now be described in detail. The handle 11 comprises right and left handle portions 140 and 141 secured together by appropriate peripheral lap joints, as shown at 142 in FIG. 4, and suitable hollow post and pin connection (not shown) respectively integral with the portions 140, 141.

The firing knob 18 is mounted externally of the handle portion 140 and has legs 146 extending therethrough for engagement with a cable pulley or spool 147. As shown in FIG. 4, spool 147 includes a depending shank 148 which is externally threaded. An internally threaded nut 149 is mounted on the shank 148. Nut 149 has a plurality of peripheral teeth 150 on the outer circumference thereof.

Handle portion 141 is provided with a circumferential array 151 of tooth receiving receptacles surrounding an upstanding post 152. When the right and left handle portions 140 and 141 are joined together, the shank 148 fits over the upstanding post 152 with the nut 149 residing on the shank 148 and the teeth 150 residing in the various receptacles of the array 151. Accordingly, when the firing knob 18 is turned, spool 147 and shank 148 also turn. Since the nut 149 is held against turning by virtue of the array 151, the nut translates or moves along the shank 148.

When the handle 11 is assembled, the nut 149 is originally placed on the shank 148 tightly against the bottom of the spool 147, as shown in FIG. 4. Accordingly, rotation of the firing knob 18 in a counterclockwise direction (as viewed in FIG. 1) is not possible since that direction of rotation would cause the nut 149 to move upwardly even more tightly against the spool 147. Since the nut 149 is restrained from rotating and engages the spool 147, the spool 147 comprises a stop means which impedes further movement of the nut 149 along the shank 148 toward the spool 147. Accordingly, it is impossible to initially rotate the firing knob 145 in an undesirable or inoperative direction. On the other hand, if the firing knob 18 is rotated in a clockwise direction, as shown in FIG. 1 in the direction of the arrow 19, the pulley 147 and the shank 148 are rotated, with the nut 149 moving downwardly toward the bottom of handle portion 141. The threads on the shank 148 are constructed so that the nut 149 reaches the bottom of the handle portion 141 just after the wedge has engaged all the drivers and all of the staples have been fired, formed and clinched, thus preventing further rotation of the firing knob 18 and signalling the stapling operation has been completed.

Of course, it will be appreciated that the spool 147 includes a receptacle means 155 for receiving the end 156 of the cable 27 such that when the spool 147 is rotated, the cable is wrapped around the spool, pulling the cable within the handle 11. It will also be appreciated that the flexible conduit 26 is secured within the receptacle 157 of handle 11 so that the conduit 26 cannot move within the handle 11. Thus the cable 27 is pulled through the conduit 26 upon rotation of knob 18 and spool 147, thereby pulling the wedge 90 through path P in the cartridge body 35. Moreover, it will be appreciated that the forward end 29 of the flexible conduit 26 is provided with an adapter 158 for securing the conduit 26 to the cartridge means 14, and preventing the cartridge means 14 from being drawn toward handle 11.

Also it will be appreciated that when the firing knob 18 is rotated in a clockwise direction, the cable 27 wraps around pulley 147 and is pulled through the conduit 26, thus pulling the wedge 90 through the cartridge body 35. This causes the wedge surface 93 to sequentially engage the drivers 40 and fire the staples from the cartridge body 35 against the anvil 103 and through any tissue which is captured in the gap G between the cartridge means 14 and the anvil means 15.

Also provided within handle 11 is a safety for preventing any rotation of the firing knob 18 and the spool 147 until such is desired. This safety is perhaps best shown in FIG. 3 and comprises a safety lug 165 and a safety slide switch 166. Switch 166 is connected to the lug 165 for moving the lug forwardly and backwardly, in the direction of the arrow A as shown in FIG. 3. The spool 147 is provided with a depending circumferential flange 167 having a lug receiving recess or cut-out 168 slightly larger than safety lug 165. Accordingly, forward motion of switch 166 urges the lug 165 into the recess or cut out 168 in the flange 167, and prevents rotation of spool 147 in any direction. Accordingly, the stapler cannot be operated until the switch 166 is moved rearwardly, withdrawing the lug 165 from the spool 147. This prevents inadvertent firing of the stapler.

OPERATION

It will be appreciated that the stapler 10, according to a preferred embodiment of the invention, is manufactured and provided with a single load of staples S and S-1 disposed in the cartridge means 14 and in the two staggered rows 61, 62 as described, with the drivers 40 poised on top of the respective staples S-1 and S.

Figure 9:
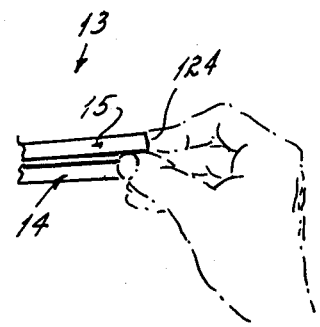
FIG. 9 is a perspective view illustrating release of the anvil cartridge latch.

Turning now to FIGS. 9-12, it will be appreciated that the cartridge means 14 and the anvil means 15 may originally be secured together. When it is desired to utilize the stapler, the button 124 is manually depressed, as shown in FIG. 9, whereupon the cartridge means 14 and anvil means 15 can be pivoted to an open position. In this regard, a detent (not shown) may be provided in the anvil support channel for cooperating with a projection on the lugs 38 and 39 in order to maintain the anvil at about a 40° open relationship with respect to the cartridge means 14.

Figure 10:
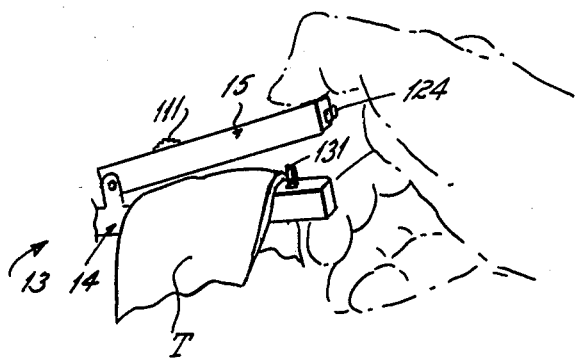
FIG. 10 is a perspective view illustrating tissue, such as an intestine, being placed in the stapler and the stapler being closed with one hand.

Thereafter, tissue such as intestinal tissue T, as shown in FIG. 10, is inserted between the cartridge means 14 and the anvil means 15. The cartridge means 14 and anvil means 15 are then pivoted about pivot point 16 until the latching lug 131 is received within the recess 133, and is latched by the latch 120.

Figure 11:
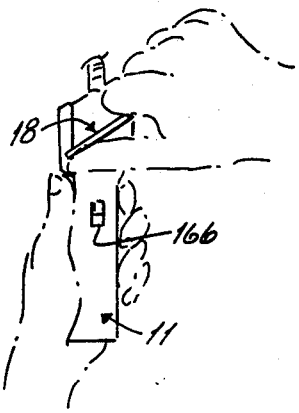
FIG. 11 is a perspective view illustrating operation of the firing knob.

The safety switch 166 is then moved rearwardly to unlock the spool 147 and the firing knob 18 is rotated in a clockwise direction, as shown in FIG. 11, to pull the flexible cable 27 into the handle.

When the cable 27 is pulled toward the handle 11, it pulls the wedge 90 along the path P within the cartridge body 35, whereupon the wedge surface 93 engages the cam surfaces, such as surfaces 45 on the respective drivers 40. As each driver is engaged, it progressively fires a staple S and a staple S-1 across the gap G between the cartridge means 14 and the anvil means 15 through any tissue T therebetween and against the anvil 103 for forming and clinching the staples S and S-1. It will be appreciated that the staple driving is accomplished in a sequential fashion and while each driver drives two staples, all staples are not driven simultaneously but rather sequentially as the wedge 90 is moved through the path P to sequentially engage the respective drivers 40. Thus, all drivers are not simultaneously operated and firing force is reduced as compared to the force which may be necessary to simultaneously fire, implant, form and clinch all staples S and S-1.

Once the safety switch 166 has been moved rearwardly, the spool 147 would ordinarily be free for rotation in either direction. Thus it would be possible to rotate the firing knob in an undesirable counterclockwise direction. The proper initial rotation direction, however, is assured by the travelling nut 149, since a resistance is encountered in turning the firing knob 18 in a counterclockwise direction due to the engagement of the nut 149 against the bottom of the spool 147. Accordingly, only proper clockwise direction is permitted in order that the spool 147 is properly rotated to pull the cable 27 and thus the wedge in order to fire the staples S and S-1.

Figure 12:
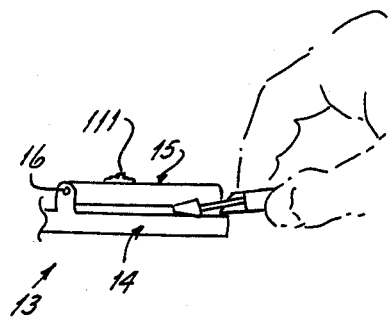
FIG. 12 is a perspective view illustrating the excision of tissue from other closed tissue in the stapler.

After the stapler 10 has been fired, and all staples S and S-1 implanted, formed and clinched in tissue T, the tissue can be excised by use of a scalpel as shown in FIG. 12. The cartridge means 14, anvil means 15, or both, can be used as a scalpel guide insuring that no excision is made too close to the implanted staples.

Thereafter, button 124 is pinched to release the forward end 57 of cartridge means 14 from anvil means 15.

The cartridge means 14 and anvil means 15 are then pivoted apart to release the closed tissue.

It will be thus appreciated that the invention provides many advantages. For example, the handle 11 can be provided independently of the cartridge means 14 and anvil means 15, thus permitting the utilization of the stapler 10 in very limited access areas where the handle 11 can remain spaced from the area. It is only necessary to maneuver the cartridge and anvil structure into the area for utilization with particular tissue. Also it will be appreciated that since the cartridge means 14 and anvil means 15 can be essentially operated with one hand, further access and utility in limited access areas is facilitated.

Also, it will be appreciated that the cam adjustment means as described herein with respect to the anvil means 15 provides for a disposable, linear, flexible surgical stapler 10 having at least two different gap settings, so that different types and sizes of tissue can be accommodated, all while the anvil means 14 and cartridge means 15 are maintained in a parallel relationship. Accordingly, single size staples can be utilized for variable gap settings and it is not necessary, within the operating range of the apparatus 10, to provide different size staples, or staplers pre-loaded with different size staples.

It will also be appreciated that the structure of the flexible stapler 10, as disclosed herein, provides for the utilization of optimum materials. For example, the cartridge housing 37 can be manufactured of metallic material, while remaining portions of the cartridge means 14 can be manufactured from plastic materials, at reduced expense, with greater manufacturing ease, and no sacrifice in strength or efficiency.

Also it will be appreciated that the position lug 130 and the position and latch lug 131 can also be manufactured from any suitable materials and as well serve to maintain the cartridge means 14 and the anvil means 15 in proper longitudinal and lateral position with respect to each other during a stapling procedure.

It should be appreciated that the structure of the drivers 40 provides the advantage of a single driver serving to fire staples in two staggered staple rows. The driver 40 is also reversible so that it fits into the driver channel 82 regardless of which leg 41 or 42 is oriented forwardly and which rearwardly. This universality is provided in part by the double cam surfaces 45, 46.

Moreover, it will be appreciated that the construction of the cartridge body means 14, drivers 40, wedge 90, handle 11, shaft 12, and the anvil means 15, all as described, might be modified, yet still produce the results as described herein.

These and other advantages and modifications will become readily apparent to those of ordinary skill in the art without departing from the scope of this invention and the applicants intend to be bound only the by the claims appended hereto.

We claim:

1. A disposable linear surgical stapler for implanting at least one row of staples in tissue, and including an anvil means for forming and clinching staples, and a staple cartridge means for driving staples across a gap toward said anvil means, said staple cartridge means including:
   a cartridge body;
   a plurality of paired staple channels in said body;
   a plurality of staple drivers comprising staple driver leg members;
   a staple driver leg member disposed in operative relation to each pair of staple channels;
   a wedge means movable through a path in which said drivers lie for engaging and moving said drivers to sequentially fire said staples;
   a flexible cable attached to said cable and means for applying tension to said cable for pulling said wedge through said path and firing said staples; and
   wherein each of said drivers is bifurcated and has two offset staple driving leg members, joined at an upper portion thereof, said upper portion defining a tapered cam surface for engagement by said wedge.

2. A disposable linear surgical stapler for implanting and forming at least one row of staples in tissue and including an anvil means for forming and clinching staples, and a staple cartridge means for driving staples therefrom across a gap and toward said anvil means, said anvil means including:
   an anvil housing secured against motion with respect to said cartridge means;
   an anvil slidably mounted in said housing and defining a plurality of staple pockets for forming and clinching staples in tissue; and
   cam means in said housing for moving said anvil with respect to said cartridge means such that said gap is adjustable.

3. A disposable linear surgical stapler comprising:
   a handle;
   an anvil means;
   a staple cartridge means;
   said staple cartridge means operatively connected to said anvil means, and said anvil means and said cartridge means selectively juxtaposed with respect to each other across a gap;
   a first staple firing means on said handle;
   second staple firing means in said staple cartridge means;
   said handle being spaced from said anvil means and said staple cartridge means;
   a flexible means operably interconnecting said staple firing means on said handle and said staple cartridge for driving staples from said cartridge toward and against said anvil across said gap;
   said flexible means comprising a flexible conduit operatively connected at one end to said handle and at another end to said staple cartridge, and a flexible cable extending through said conduit, said flexible cable connected at one end to said first staple firing means and at an another end to said second staple firing means for pulling said second staple firing means, upon actuation of said first staple firing means, through said staple cartridge means to fire said staples; and
   wherein said staple firing means is operable to fire staples seriatim in at least one row.

4. A disposable linear surgical stapler, as in claim 3, wherein said anvil means includes an anvil having a plurality of staple receiving and clinching pockets and means for adjusting said anvil toward and away from said staple cartridge means for varying said gap, said adjusting means being operationally independent of said handle and said first staple firing means.

5. A disposable linear surgical stapler for implanting and forming at least one line of staples in tissue and comprising:
   a handle;

an anvil means including an anvil having a plurality of staple pockets for forming and clinching staples;

a staple cartridge means including a plurality of staple channels for holding staples in a row, said staple cartridge means operatively juxtaposed with said anvil means;

said handle being spaced from said anvil means and said cartridge means;

a plurality of staple drivers operatively aligned with respective staples in said staple channels;

a driver engaging wedge means disposed at a forward end of said staple cartridge and movable in a drive path therein for sequentially engaging said drivers, moving them toward said staples and firing said staples from said channels toward said anvil;

a flexible conduit extending between said handle and said cartridge means;

a rotatable firing knob means in said handle; and a flexible cable extending through said conduit and having a forward end attached to said wedge means, and a rearward end attached to said firing knob means such that rotation of said knob means pulls said cable and said wedge is thereby pulled through said path, serially engaging said drivers and firing said staples.

6. A disposable linear surgical stapler, as in claim 5, wherein said anvil means is pivoted to said cartridge means and juxtaposed in a parallel operative relationship therewith, defining a gap therebetween.

7. A disposable linear surgical stapler, as in claim 6, wherein said anvil means includes an anvil housing and anvil position adjusting means in said housing, independent of said handle and said rotatable firing knob means, for adjusting the position of said anvil with respect to said housing and in a direction to vary the width of said gap between said anvil means and said cartridge means.

8. A disposable linear surgical stapler, as in claim 7, wherein said anvil housing is pivoted at one end to said cartridge means and includes a releasable cartridge latch means disposed at another end thereof.

9. A disposable linear surgical stapler, as in claim 8, wherein said anvil includes a cartridge means positioning receptacle at each end thereof for receiving cartridge positioning and latching projections for positioning said cartridge means with respect to said anvil.

10. A disposable linear surgical stapler, as in claim 5, wherein said stapler is operable to implant and form two staggered rows of staples in tissue and further including a plurality of staggered guide rails within said cartridge means and defining driver channels for guiding said staple drivers as they are moved by said wedge means to fire said staples, said staggered guide rails also defining inwardly facing guide surfaces for guiding said wedge means along said path.

11. A disposable linear surgical stapler, as in claim 10, further including a wedge means pocket disposed at a forward end of said cartridge means receiving said wedge means prior to movement thereof along said path.

12. A disposable linear surgical stapler, as in claim 11, wherein guide rails at a forward end of said path within said cartridge means have respective forward tapering surfaces leading from said wedge means pocket to said path for guiding said wedge therebetween when said wedge is pulled toward said drivers.

13. A disposable linear surgical stapler, as in claim 12, wherein each of said drivers comprises bifurcated, offset, staple driving leg portions, joined at upper ends thereof, each upper end having a cam surface sloping upwardly to an apex intermediate said leg portions.

14. A disposable linear surgical stapler, as in claim 5, wherein said anvil means and said cartridge means are pivoted together at a pivot point near rearward ends thereof, and said anvil means comprises an anvil having two ends, each defining a cartridge positioning receptacle.

15. A disposable linear surgical stapler, as in claim 14, wherein said cartridge means includes a positioning lug extending outwardly of said cartridge means disposed near the pivot point, and positioned to enter one of said cartridge positioning receptacles when said anvil means and cartridge means are pivoted together, and wherein said cartridge means further includes a latching and positioning lug at a forward end thereof, said latching and pivoting lug extending into another of said cartridge positioning receptacles when said anvil means and said cartridge means are pivoted together, for positioning said cartridge means and said staple channels in operative position with respect to said anvil means and said staple pockets therein.

16. A disposable linear surgical stapler, as in claim 15, further including latching means disposed at a forward end of said anvil means for receiving and releasably latching said latching and positioning lug.

17. A disposable linear surgical stapler, as in claim 5, wherein said flexible conduit has two ends, one secured to said handle and one to said cartridge means, such that when said knob means is operated, said cable is slidable within said conduit and is operative to draw said wedge means within said cartridge means from a forward to a rearward end thereof and toward said handle.

18. A disposable linear surgical stapler having a cartridge means and an anvil means cooperating for implanting staples in tissue therebetween, a handle independent of said cartridge means and said anvil means, and a flexible drive shaft means, including a flexible cable for operating said cartridge means to fire a number of staples toward said anvil means, said handle including:

a rotatable firing knob;

a cable spool mounted for rotation with said knob and operable to pull said cable when initially rotated in a predetermined direction; and, means for preventing initial rotation of said spool in an inoperative direction other than said predetermined direction.

19. A disposable linear surgical stapler comprising:

a handle;

an anvil means;

a staple cartridge means containing a plurality of staples in at least one straight row;

said staple cartridge means operatively connected to said anvil means, and said anvil means and said cartridge means selectively juxtaposed with respect to each other across a gap;

a staple firing means on said handle;

a slidable staple firing wedge disposed within said staple cartridge means at one end thereof and being selectively movable in a path adjacent said staples in said one straight row;

said handle being spaced from said anvil means and said staple cartridge means;

a flexible means including a flexible conduit and a flexible cable therein, said flexible cable operably interconnecting said staple firing means on said handle and said staple cartridge at another end of said staple cartridge means for pulling said firing wedge along said path and for driving staples from said cartridge toward and against said anvil across said gap;

said firing wedge being initially disposed at said one end of said staple cartridge means and being slidable through said path toward each other end of said staple cartridge means; and wherein said staple firing means is operable to fire staples serially in a straight row.

20. A disposable linear surgical stapler comprising:
a handle;
an anvil means;
a staple cartridge means containing a plurality of staples;
said staple cartridge means operatively connected to said anvil means, and said anvil means and said cartridge means selectively juxtaposed with respect to each other across a gap;
a staple firing means on said handle;
a slidable staple firing wedge disposed at one end of said staple cartridge means and being slidable through a path adjacent and along said plurality of staples;
said handle being spaced from said anvil means and said staple cartridge means;
a flexible means, comprising a flexible conduit and a flexible cable extending therethrough, operably interconnecting said staple firing means on said handle and said staple cartridge and being connected to said firing wedge for pulling said wedge through said path for driving staples from said cartridge toward and against said anvil across said gap; and
wherein said staple firing means, said flexible means and said firing wedge are operable to fire staples serially.

21. A disposable linear surgical stapler for implanting and forming at least one line of staples in tissue and comprising:
a handle;
an anvil means including an anvil having a plurality of staple pockets for forming and clinching staples;
a staple cartridge means including a plurality of staple channels for holding staples in a row, said staple cartridge means operatively juxtaposed with said anvil means;
said anvil means being pivoted to said cartridge means and juxtaposed in a parallel operative relationship therewith, defining a gap therebetween;
said anvil means further including an anvil housing and anvil position adjusting means in said housing for adjusting the position of said anvil with respect to said housing and in a direction to vary the width of said gap between said anvil means and said cartridge means;
said anvil position adjusting means including a sliding cam having two cam surfaces corresponding to a retracted anvil position and two second cam surfaces corresponding to a projected anvil position and a smaller gap;
said handle being spaced from said anvil means and said cartridge means;
a plurality of staple drivers operatively aligned with respective staples in said staple channels;
a driver engaging wedge means disposed at a forward end of said staple cartridge and movable in a drive path therein for sequentially engaging said drivers, moving them toward said staples and firing said staples from said channels toward said anvil;
a flexible conduit extending between said handle and said cartridge means;
a rotatable firing knob means in said handle; and
a flexible cable extending through said conduit and having a forward end attached to said wedge means, and a rearward end attached to said firing knob means such that rotation of said knob means pulls said cable and said wedge is thereby pulled through said path, sequentially engaging said drivers and firing said staples.

22. A disposable linear surgical stapler, as in claim 21, including two screws mounted in an upper face of said anvil rearward of said staple pockets, said screws having heads disposed in sliding engagement with said sliding cam and respective cam surfaces, said screws being rotatable within said anvil for adjustment of the position of said anvil with respect to said sliding cam and said anvil housing.

23. A disposable linear surgical stapler, as in claim 22, further including a retention plate connected to said sliding cam for motion therewith and including a slot at each end through which a respective one of said screws extends.

24. A disposable linear surgical stapler for implanting and forming at least one line of staples in tissue and comprising:
a handle;
an anvil means including an anvil having a plurality of staple pockets for forming and clinching staples;
a staple cartridge means including a plurality of staple channels for holding staples in a row, said staple cartridge means operatively juxtaposed with said anvil means;
said handle being spaced from said anvil means and said cartridge means;
a plurality of staple drivers operatively aligned with respective staples in said staple channels;
a driver engaging wedge means disposed at a forward end of said staple cartridge and movable in a drive path therein for sequentially engaging said drivers, moving them toward said staples and firing said staples from said channels toward said anvil;
a flexible conduit extending between said handle and said cartridge means;
a rotatable firing knob means in said handle;
a flexible cable extending through said conduit and having a forward end attached to said wedge means, and a rearward end attached to said firing knob means such that rotation of said knob means pulls said cable and said wedge is thereby pulled through said path, sequentially engaging said drivers and firing said staples, wherein said stapler is operable to implant and form two staggered rows of staples in tissue and further including;
a plurality of staggered guide rails within said cartridge means and defining driver channels for guiding said staple drivers as they are moved by said wedge means to fire said staples, said staggered guide rails also defining inwardly facing guide surfaces for guiding said wedge means along said path;
a wedge means pocket disposed at a forward end of said cartridge means receiving said wedge means prior to movement thereof along said path;
said guide rails at a forward end of said path within said cartridge means having respective forward tapering surfaces leading from said wedge means pocket to said path for guiding said wedge therebetween when said wedge is pulled toward said drivers;

each of said drivers comprising bifurcated, offset, staple driving leg portions, joined at upper ends thereof, each upper end having a cam surface sloping upwardly to an apex intermediate said leg portions; and wherein one of said leg portions of each driver resides between two of said guide rails on one side of said cartridge means and said path and the other leg portion of each driver resides between another two guide rails on another side of said cartridge means and said path and offset from said first two projection means.

25. A disposable linear surgical stapler, as in claim 24, including an elongated driver blocking rib extending between staple rows at a bottom face of said cartridge means for blocking free movement of drivers out of said cartridge means.

26. A disposable linear surgical stapler, as in claim 25, including a cartridge lid disposed over said driver channels and capturing said drivers therein, said lid having therein an elongated slot aligned with said path for guiding said wedge means, said wedge means being moveable in a direction extending between ends of said elongated slot.

27. A disposable linear surgical stapler, as in claim 26, wherein said wedge means includes a tapered wedge blade extending through said elongated slot in said path and a base member slidably disposed on said cartridge lid, said lid extending between said base member and said drive path.

28. A disposable linear surgical stapler, as in claim 27, wherein said cartridge means includes a cartridge body housing said staple channels, guide rails, drivers and wedge pocket, and further including a cartridge housing enclosing said base member of said wedge means and slidably holding said base member on said cartridge lid.

29. A disposable linear surgical stapler for implanting and forming at least one line of staples in tissue and comprising:
a handle;
an anvil means including an anvil having a plurality of staple pockets for forming and clinching staples;
a staple cartridge means including a plurality of staple channels for holding staples in a row, said staple cartridge means operatively juxtaposed with said anvil means;
said handle being spaced from said anvil means and said cartridge means;
a plurality of staple drivers operatively aligned with respective staples in said staple channels;
a driver engaging wedge means disposed at a forward end of said staple cartridge and movable in a drive path therein for sequentially engaging said drivers, moving them toward said staples and firing said staples from said channels toward said anvil;
a flexible conduit extending between said handle and said cartridge means;
a rotatable firing knob means in said handle;
a flexible cable extending through said conduit and having a forward end attached to said wedge means, and a rearward end attached to said firing knob means such that rotation of said knob means pulls said cable and said wedge is thereby pulled through said path, sequentially engaging said drivers and firing said staples, and includes:
a knob;
a cable spool attached to said knob for rotation therewith;
a threaded shank extending beyond said spool for rotation therewith;
a nut on said threaded shank;
means for restraining said nut from rotation, such that when said knob is turned said nut moves along said shank; and
first stop means for engaging said nut, and preventing rotation of said knob in an inoperative direction when said knob is initially rotated.

30. A disposable linear surgical stapler, as in claim 29, wherein said cable spool is provided with a safety lug recess and further including a slidable safety lug within said handle for extending into said safety lug recess in a safety position preventing rotation of said knob, and being slidable out of said safety lug recess to permit rotation of said knob.

31. A disposable linear surgical stapler for implanting and forming at least one line of staples in tissue and comprising:
a handle;
an anvil means including an anvil having a plurality of staple pockets for forming and clinching staples;
a staple cartridge means including a plurality of staple channels for holding staples in a row, said staple cartridge means operatively juxtaposed with said anvil means;
said handle being spaced from said anvil means and said cartridge means;
a plurality of staple drivers operatively aligned with respective staples in said staple channels;
a driver engaging wedge means disposed at a forward end of said staple cartridge and movable in a drive path therein for sequentially engaging said drivers, moving them toward said staples and firing said staples from said channels toward said anvil;
a flexible conduit extending between said handle and said cartridge means;
a rotatable firing knob means in said handle;
a flexible cable extending through said conduit and having a forward end attached to said wedge means, and a rearward end attached to said firing knob means such that rotation of said knob means pulls said cable and said wedge is thereby pulled through said path, sequentially engaging said drivers and firing said staples;
said flexible conduit having two ends, one secured to said handle and one to said cartridge means, such that when said knob means is operated, said cable is slidable within said conduit and is operative to draw said wedge means within said cartridge means from a forward to a rearward end threof and toward said handle; and
further including a flexible reinforcing means attached along said conduit for preventing firing of said staples in response to inadvertent elongation of said flexible conduit.

32. A disposable linear surgical stapler having a cartridge means and an anvil means cooperating for implanting staples in tissue therebetween, a handle independent of said cartridge means and said anvil means, and a flexible drive shaft means, including a flexible cable for operating said cartridge means to fire a number of staples toward said anvil means, said handling including:
- a rotatable firing knob;
- a cable spool mounted for rotation with said knob and operable to pull said cable when initially rotated in a predetermined direction; and,
- means for preventing initial rotation of said spool in an inoperative direction other than said predetermined direction;
- wherein said means for preventing initial rotation of said spool in an inoperative direction includes a threaded shank attached to said spool for rotation therewith, a nut mounted on said shank, means to restrain said nut against rotation so that said nut moves linearly along said shank when said knob, spool and shank are rotated, and a stop surface holding said nut against such linear movement, and holding said shank, spool and knob against rotation in a predetermined inoperative direction.

33. A disposable linear surgical stapler, as in claim 32, further including a second stop surface for preventing continued rotation of said shank, spool and knob when said number of staples has been fired.

34. A disposable linear surgical stapler, as in claim 32, further including slidable safety lug means for engaging one of said knob, spool and shank and selectively preventing rotation thereof.

* * * * *